United States Patent [19]

Ogawa et al.

[11] Patent Number: 4,640,795
[45] Date of Patent: Feb. 3, 1987

[54] 5-ALKYL-2-(3,4-DIFLUOROPHENYL)-PYRIMIDINE AND NEMATIC LIQUID CRYSTAL COMPOSITION CONTAINING SAME

[75] Inventors: Tetsuya Ogawa; Kisei Kitano; Yasuyuki Goto; Masahiro Fukui, all of Yokohamashi; Shigeru Sugimori, Fujisawashi, all of Japan

[73] Assignee: Chisso Corporation, Osaka, Japan

[21] Appl. No.: 842,190

[22] Filed: Mar. 21, 1986

[51] Int. Cl.⁴ .................... C09K 19/34; G02F 1/13; C07D 239/00
[52] U.S. Cl. ..................... 252/299.5; 252/299.61; 350/350 R; 544/242; 544/319; 544/335
[58] Field of Search .............. 252/299.5, 299.61; 350/350 R; 544/319, 335, 242

[56] References Cited

U.S. PATENT DOCUMENTS

| 4,512,636 | 4/1985 | Andrews et al. | 252/299.61 |
| 4,533,488 | 8/1985 | Fukui et al. | 252/299.61 |
| 4,581,155 | 4/1986 | Goto et al. | 252/299.61 |

FOREIGN PATENT DOCUMENTS

| 84194 | 7/1983 | European Pat. Off. | 252/299.61 |
| 123907 | 11/1984 | European Pat. Off. | 252/299.61 |
| 2257588 | 6/1973 | Fed. Rep. of Germany | 252/299.61 |
| 3315295 | 10/1984 | Fed. Rep. of Germany | 252/299.61 |
| 59-184165 | 10/1984 | Japan | 252/299.61 |
| 59-216876 | 12/1984 | Japan | 252/299.61 |
| 60-54371 | 3/1985 | Japan | 252/299.61 |
| 60-78972 | 5/1985 | Japan | 252/299.61 |

Primary Examiner—Teddy S. Gron
Attorney, Agent, or Firm—Leydig, Voit & Mayer

[57] ABSTRACT

A novel compound which exhibits superior effectiveness particularly in reducing the driving voltage of liquid crystal display elements, and a liquid crystal composition containing the same are provided, which compound is a 5-alkyl-2-(3,4-difluorophenyl)pyrimidine expressed by the formula

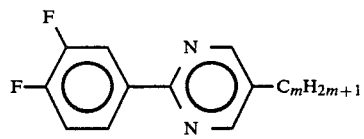

wherein m represents an integer of 1 to 8.

9 Claims, 4 Drawing Figures

5-ALKYL-2-(3,4-DIFLUOROPHENYL)PYRIMIDINE AND NEMATIC LIQUID CRYSTAL COMPOSITION CONTAINING SAME

BACKGROUND OF THE INVENTION

1. Field of the Invention

This invention relates to a fluorine-containing pyrimidine derivative suitable as a component of liquid crystal compositions used in liquid crystal display devices, and a liquid crystal composition containing the derivative.

2. Description of the Prior Art

As well known, liquid crystal materials used for liquid crystal display (hereinafter abbreviated to LCD) elements have been required to have per se not only chemical stability to air, moisture, etc., and physical stability to light, heat, electricity, etc., but LCD elements using the materials have also been required to hold well-balanced characteristics such as operation temperature range, operating voltage, response properties, etc. As electronics art advances, requirements for such liquid crystal materials have been becoming severer and severer in the aspect of these characteristics. Recently, liquid crystal materials capable of effecting LCD under lower operating voltage have been required.

SUMMARY OF THE INVENTION

The object of the present invention is to provide a novel compound which exhibits, as a liquid crystal component, superior effectiveness particularly for reducing the driving voltage of LCD elements.

The present invention in a first aspect resides in a 5-alkyl-2-(3,4-difluorophenyl)pyrimidine expressed by the formula

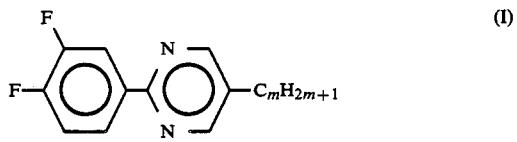

wherein m represents an integer of 1 to 8.

The present invention in a second aspect resides in a liquid crystal composition comprising at least one liquid crystal compound and at least one compound expressed by the above formula (I), each in a quantity effective as a liquid crystal component.

DESCRIPTION OF PREFERRED EMBODIMENTS

Figure 1:
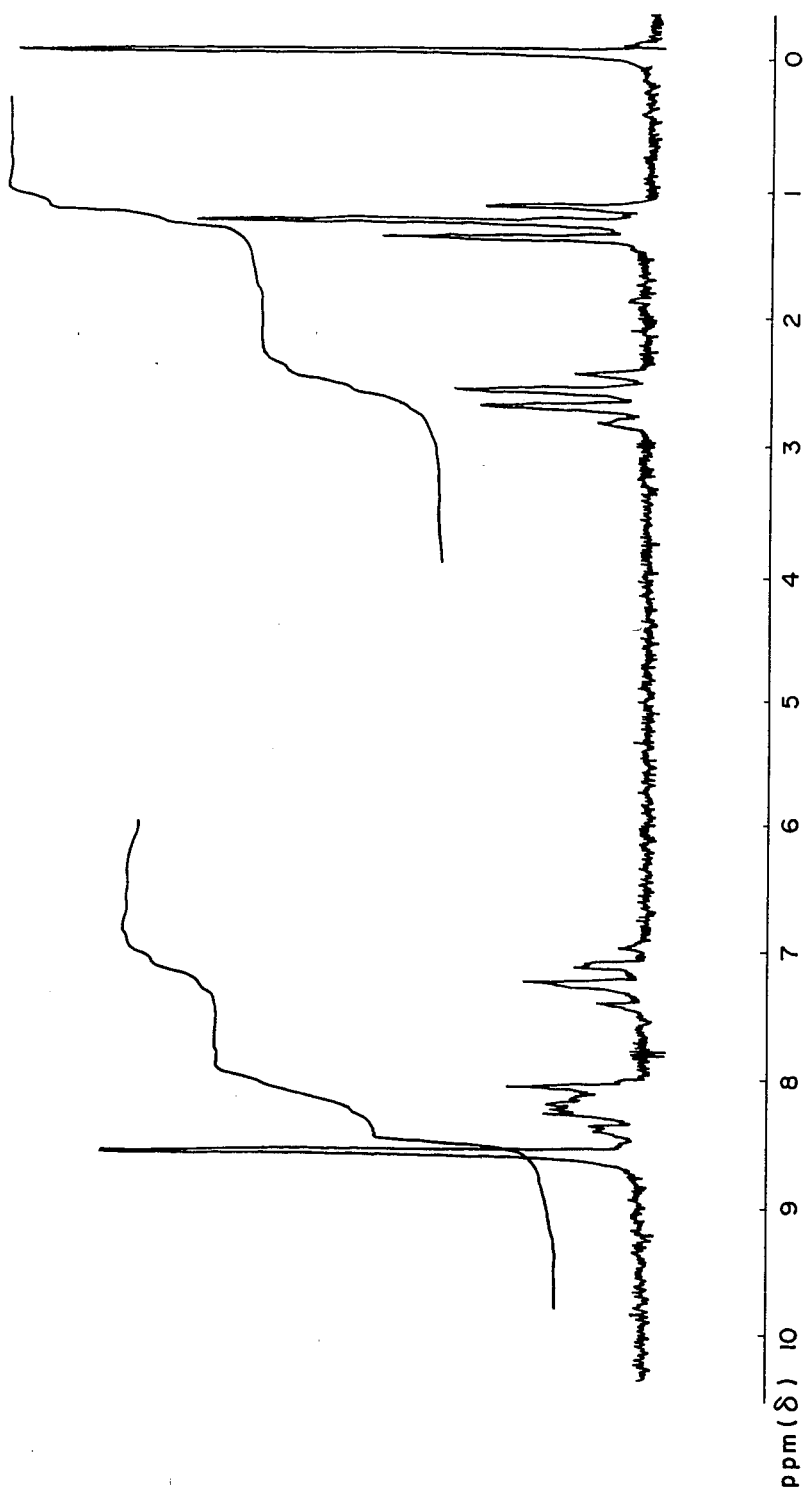
FIGS. 1, 2 and 3 each show the $^1$H-NMR chart of the compounds of the present invention of Examples described later.

Among the compounds of the present invention, the following are particularly preferred:
5-ethyl-2-(3,4-difluorophenyl)pyrimidine,
5-propyl-2-(3,4-difluorophenyl)pyrimidine,
5-butyl-2-(3,4-difluorophenyl)pyrimidine,
5-pentyl-2-(3,4-difluorophenyl)pyrimidine,
5-hexyl-2-(3,4-difluorophenyl)pyrimidine and
5-heptyl-2-(3,4-difluorophenyl)pyrimidine.

These compounds exhibit no liquid crystalline properties per se, but when they are used as a liquid crystal component, they exhibit the following specific features as in the case of other compounds of the present invention:

good compatibility with many other kinds of liquid crystal compounds; due to their low viscosity, capability of reducing the viscosity of many liquid crystal blends; increase in the dielectric anisotropy value of liquid crystal blends; and capability of reducing the driving voltage of LCD elements.

Further, compounds of the formula (I) wherein the $-C_mH_{2m+1}$ group represents a branched chain alkyl are superior in the compatibility with various liquid crystal compounds.

Preparation of the compound of the present invention may be illustrated typically by the following reaction scheme:

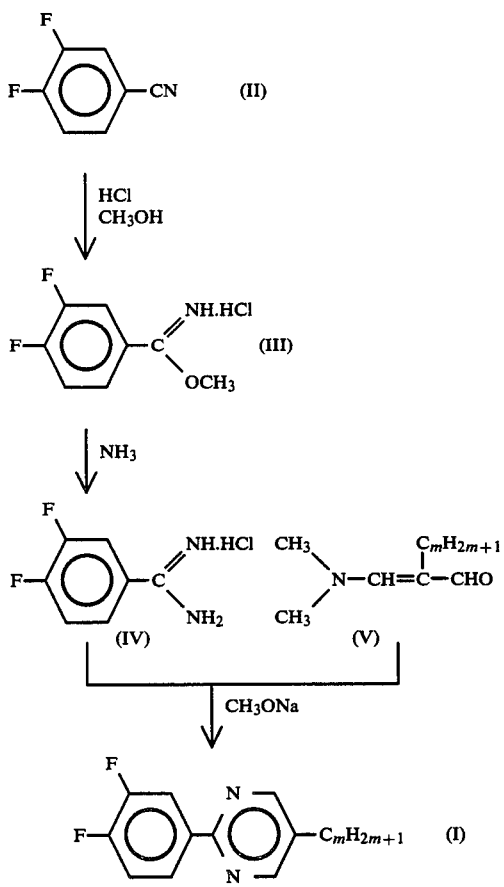

First, 3,4-difluorobenzonitrile (II) prepared by a known method is reacted with methanol and hydrogen chloride to obtain an imino-ether hydrochloride (III), followed by passing ammonia gas through an ethanol solution of (III) to obtain 3,4-difluorobenzamidine hydrochloride (IV), subjecting this (IV) and an α-alkyl-β-dimethylaminoacrolein (V) to a cyclization reaction in the presence of a basic catalyst to obtain a 5-alkyl-2-(3,4-difluorophenyl)pyrimidine (I).

In West Germany Patent application laid-open as DE No. 33 15 295 A1, a compound of the following general formula is shown, R—Z—PhF—F wherein R represents an alkyl group of 1 to 12 carbon atoms, Z, pyrimidin-2,5-diyl, and PhF, 2- or 3-fluoro-1,4-phenylene.

The disclosure of the compound in this publication, however, is insufficient in the following points.

Neither concrete compounds nor characteristic values for identifying the compounds are described therein.

In addition to the above-mentioned uncertainty, a compound of the above-described formula is shown in the published invention the aim of which is to find a stable liquid-crystalline compound as a component for a liquid-crystalline dielectric. Whereas, the present invention discloses that a 5-alkyl-2-(3,4-difluorophenyl)-pyrimidine is not a liquid crystal compound as aimed in the above publication. Non-liquid-crystalline as a compound per se of the present invention is, it exhibits a superior effectiveness in reducing the driving voltage of LCD elements employing a liquid crystal composition containing at least one compound of the present invention. This effectiveness will be shown in Examples and Comparative examples mentioned later.

The liquid crystal composition of the present invention comprises at least two components one of which contains at least one compound of the above formula (I).

As another component, there may be used compounds selected from among known liquid crystal compounds such as those of Schiff's bases, biphenyls, phenylcyclohexanes, esters, pyrimidines, dioxanes, azo or azoxy compounds, etc. These compounds or mixtures thereof may be commercially available or may be prepared according to a known method described in literatures.

The liquid crystal composition of the present invention may contain the 5-alkyl-2-(3,4-difluorophenyl)-pyrimidine expressed by the formula (I) in a quantity of 0.1 to 40% by weight, preferably 5 to 30% by weight. If the content of the non-liquid-crystalline 5-alkyl-2-(3,4-difluorophenyl)pyrimidine exceeds 40% by weight, the mesomorphic temperature range of the blend containing the same is often narrowed undesirably.

The composition may be prepared in a conventional manner, e.g. by dissolving the respective components in one another and preferably on heating.

The liquid crystal composition may have, if necessary, a dichroic dyestuff, an electroconductive salt or the like added thereto to be used in known LCD mode.

The liquid crystal composition of the present invention has superior characteristics of not only reducing the driving voltage of LCD elements using the composition, but also notably improving the temperature dependence (usually expressed by a value of $dV_{th}/dt$) of the threshold voltage of LCD elements.

The present invention will be described in more detail by way of Examples and Comparative examples.

EXAMPLE 1

Preparation of 5-ethyl-2-(3,4-difluorophenyl)pyrimidine

To a solution of sodium methoxide prepared by dissolving metallic sodium (2.8 g) dissolved in anhydrous methanol (20 cc) were added 3,4-difluorobenzamidine hydrochloride (11.6 g, 0.06 mol) and α-ethyl-β-dimethylaminoacrolein (8.9 g, 0.066 mol), followed by heating the mixture under reflux for 6 hours, thereafter distilling off methanol at the atmospheric pressure, adding toluene (20 cc) to the reaction residue to extract the product, washing the extraction solution with water, drying the toluene layer over anhydrous sodium sulfate, filtering off the drying agent, distilling off toluene, and recrystallizing the residue from ethanol (20 cc) to obtain the objective 5-ethyl-2-(3,4-difluorophenyl)pyrimidine (7.0 g) having a m.p. of 86.6° C. Its $^1$H-NMR (proton nuclear magnetic resonance) spectra are shown in FIG. 1.

EXAMPLES 2~6

Example 1 was repeated except that α-ethyl-β-dimethylaminoacrolein in Example 1 was replaced by other corresponding α-n-alkyl-β-dimethylaminoacroleins to obtain 5-n-alkyl-2-(3,4-difluorophenyl)pyrimidines shown in Examples 2~6. Their melting points are shown in Table 1 together with the results of Example 1.

TABLE 1

Figure 2:
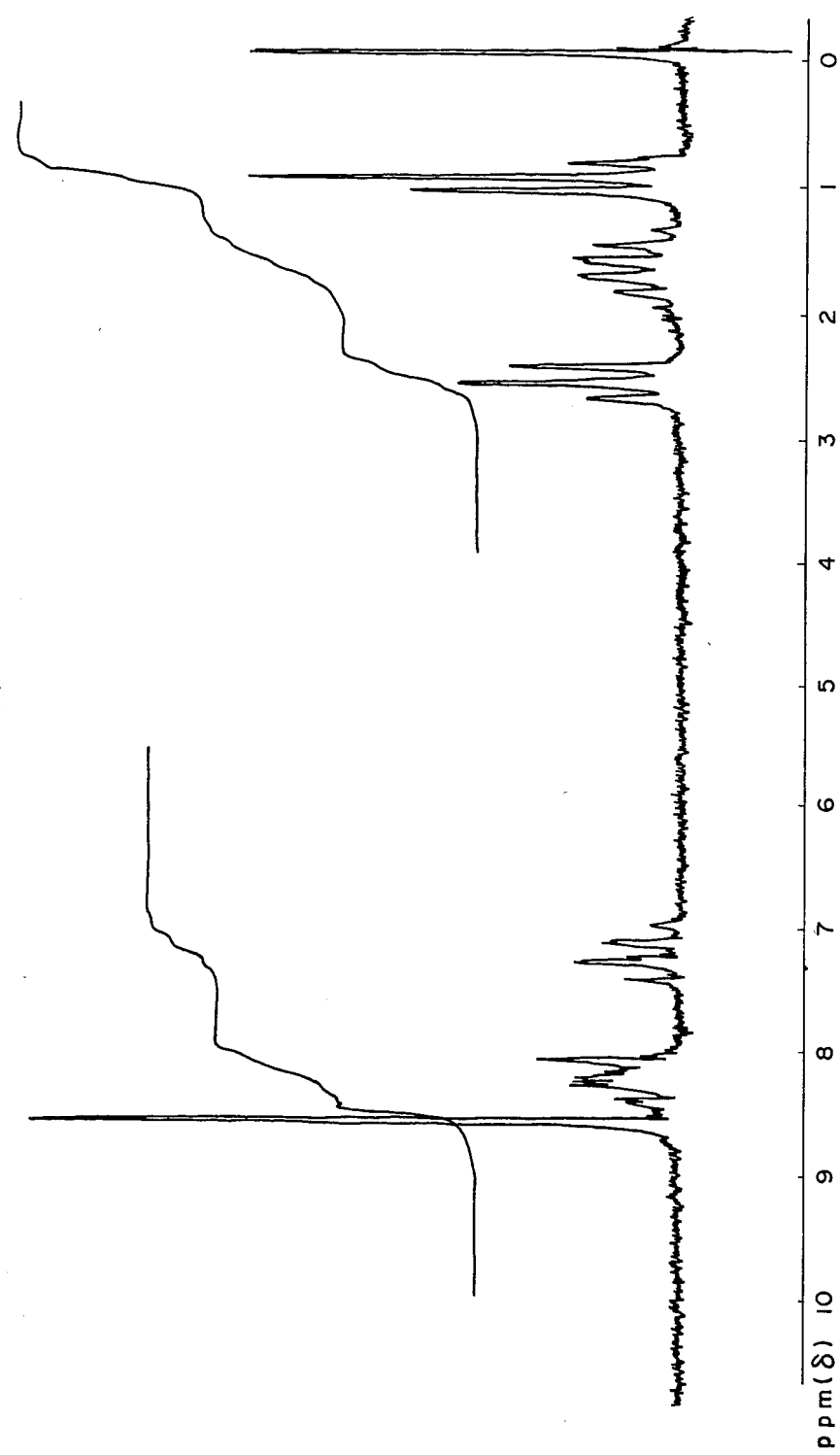
Figure 3:
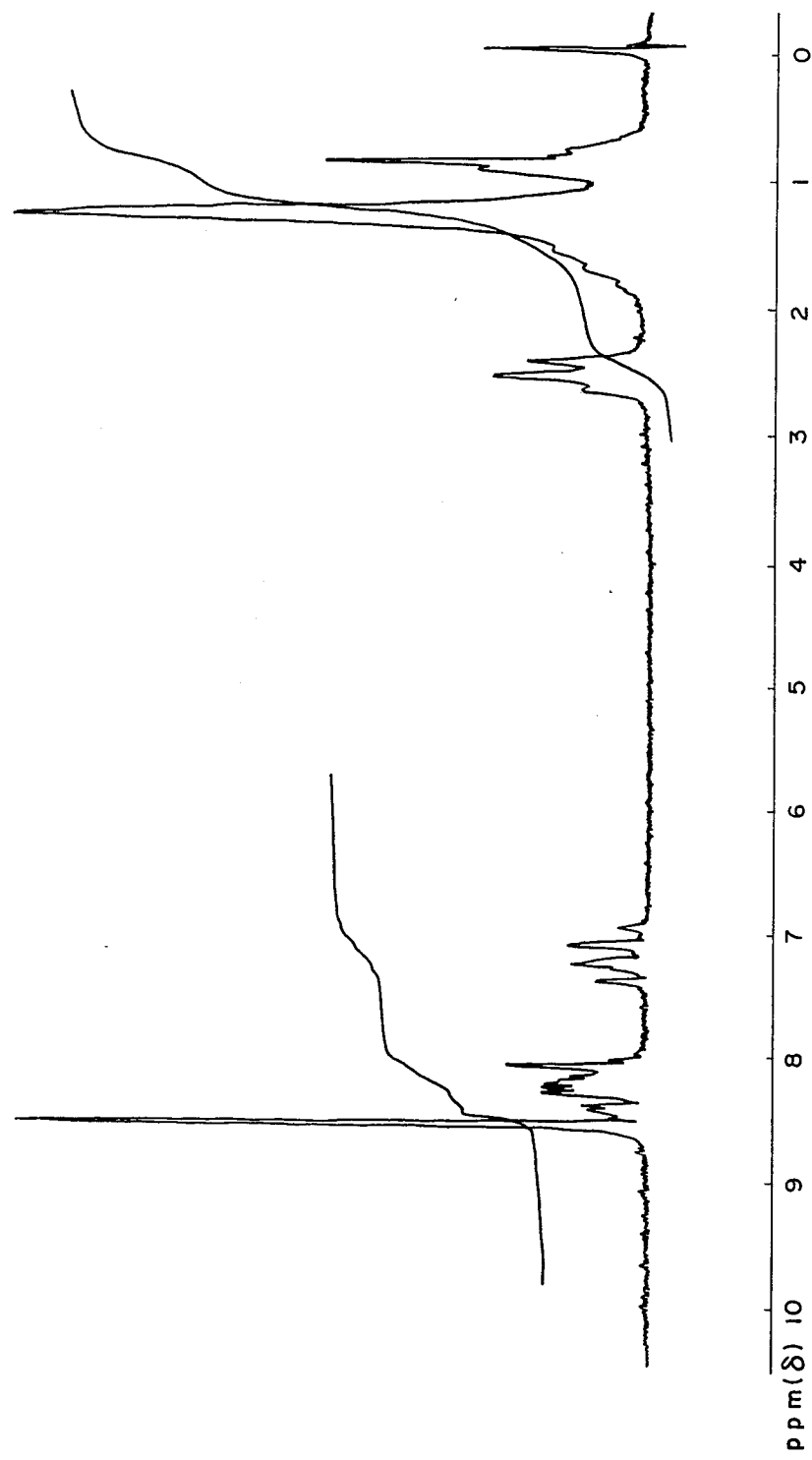

| Example | m in formula (I) | Identification data | |
|---|---|---|---|
| | | M.P.(°C.) | $^1$H—NMR |
| 1 | 2 | 86.6 | shown in FIG. 1 |
| 2 | 3 | 38.3 | shown in FIG. 2 |
| 3 | 4 | 39.6 | — |
| 4 | 5 | 15.1 | — |
| 5 | 6 | 17.1 | — |
| 6 | 7 | 4.1 | shown in FIG. 3 |

EXAMPLES 7~12

A liquid crystal composition (hereinafter referred to as base composition) consisting of trans-4-propyl-(4'-cyanophenyl)cyclohexane 26% by weight, trans-4-pentyl-(4'-cyanophenyl)cyclohexane 36% by weight, trans-4-heptyl-(4'-cyanophenyl)cyclohexane 25% by weight, and trans-4-pentyl-(4''-cyanobiphenyl)cyclohexane 13% by weight, has a viscosity at 20° C. ($\eta_{20}$) of 27.8 cP and a dielectric anisotropy value ($\Delta\epsilon$) of 11.6. When the base composition was sealed in a TN cell of 10 μm thick, the resulting cell exhibited an operating threshold voltage ($V_{th}$) of 1.75 V.

When the respective compounds (15 parts by weight) shown in Examples 1~6 of the present invention were added to the above base composition (85 parts by weight), the resulting compositions had the following $\eta_{20}$ and $\Delta\epsilon$ and also the TN cells employing the compositions exhibited the following operating threshold voltages:

TABLE 2

| Example | m in formula (I) | $\eta_{20}$ (cP) | $\Delta\epsilon$ | $V_{th}(v)$ |
|---|---|---|---|---|
| 7 | 2 | 24.7 | 14.0 | 1.26 |
| 8 | 3 | 25.4 | 12.5 | 1.34 |
| 9 | 4 | 25.9 | 12.5 | 1.34 |
| 10 | 5 | 26.2 | 12.2 | 1.37 |
| 11 | 6 | 26.5 | 12.4 | 1.27 |
| 12 | 7 | 28.1 | 12.0 | 1.38 |

COMPARATIVE EXAMPLES 1~5

The respective compounds (15 parts by weight) expressed by the formula

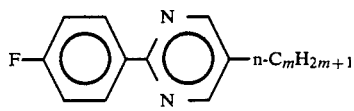

(VI)

wherein m represents 2, 3, 4, 5 or 6, were added to the above base composition (85 parts by weight). The TN cells of the resulting compositions exhibited the following operating threshold voltages:

TABLE 3

| Comparative example | m in formula (VI) | $V_{th}$ |
| --- | --- | --- |
| 1 | 2 | 1.37 |
| 2 | 3 | 1.40 |
| 3 | 4 | 1.38 |
| 4 | 5 | 1.41 |
| 5 | 6 | 1.41 |

COMPARATIVE EXAMPLES ~10

The respective compounds (15 parts by weight) expressed by the formula

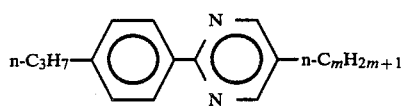

(VII)

wherein n represents 2, 3, 4, 5 or 6, were added to the above base composition (85 parts by weight). The TN cells of the resulting compositions exhibited the following operating threshold voltages:

TABLE 4

| Comparative example | m in formula (VII) | $V_{th}$ |
| --- | --- | --- |
| 6 | 2 | 1.53 |
| 7 | 3 | 1.58 |
| 8 | 4 | 1.58 |
| 9 | 5 | 1.65 |
| 10 | 6 | 1.62 |

COMPARATIVE EXAMPLES 11~16

The respective compounds (15 parts by weight) expressed by the formula

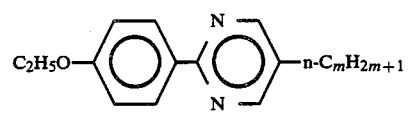

(VIII)

wherein m represents 2, 3, 4, 5, 6 or 7, were added to the above base composition (85 parts by weight). The TN cells of the resulting compositions exhibited the following operating threshold voltages:

TABLE 5

| Comparative example | m in formula (VIII) | $V_{th}$ |
| --- | --- | --- |
| 11 | 2 | 1.60 |
| 12 | 3 | 1.69 |
| 13 | 4 | 1.64 |

TABLE 5-continued

| Comparative example | m in formula (VIII) | $V_{th}$ |
| --- | --- | --- |
| 14 | 5 | 1.65 |
| 15 | 6 | 1.72 |
| 16 | 7 | 1.72 |

COMPARATIVE EXAMPLE 17

A compound expressed by the formula

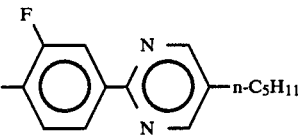

has a m.p. of 64.7° C. This compound (15 parts by weight) was added to the above base composition (85 parts by weight). The TN cells of the resulting composition exhibited an operating threshold voltage of 1.53 volt.

Figure 4:
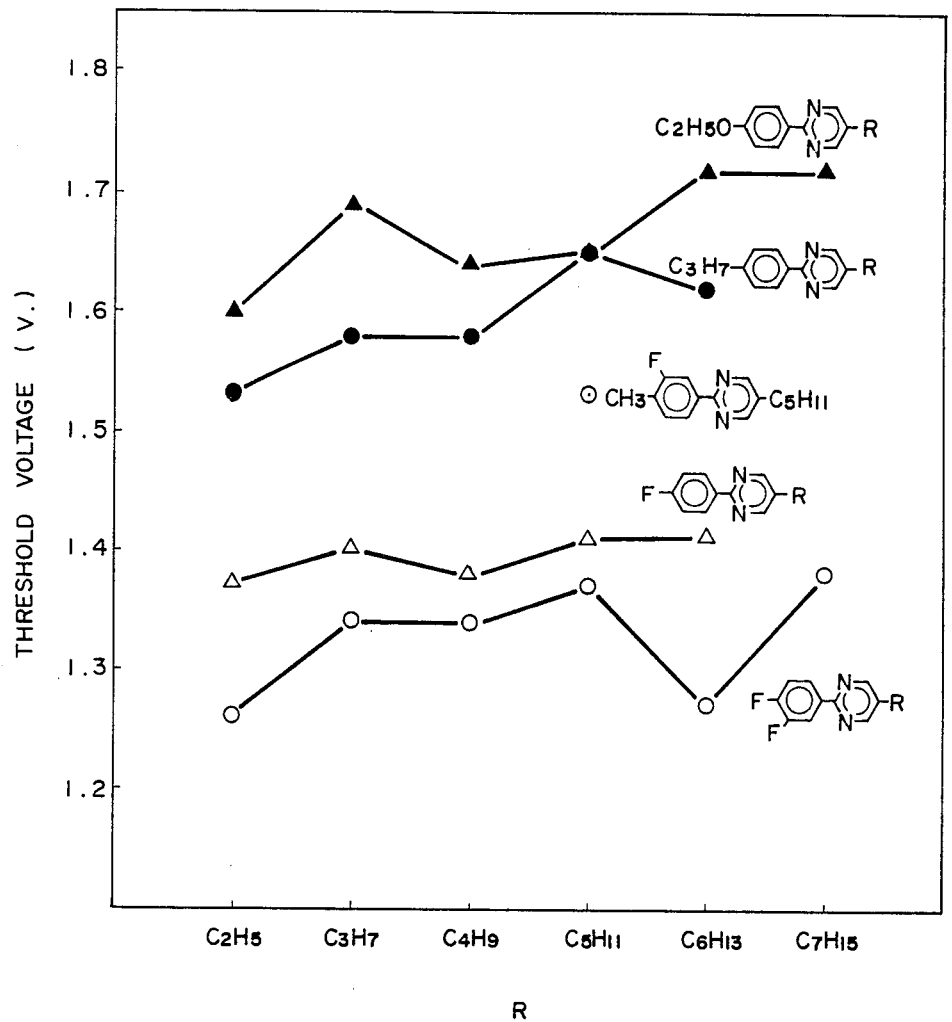
FIG. 4 shows a chart illustrating the respective operating threshold voltage of LCD elements using the liquid crystal compositions shown in Examples and Comparative examples.

The results of Examples 7 - 12 and Comparative examples 1~17 are shown in FIG. 4 for comparison. It is evident from FIG. 4 that the compound of the present invention is most effective for reducing the threshold voltage of TN cell.

What we claim is:

1. A 5-alkyl-2-(3,4-difluorophenyl)pyrimidine expressed by the formula

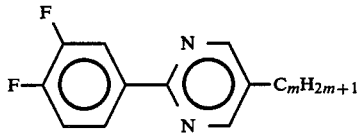

wherein m represents an integer of 1 to 8.

2. 5-Ethyl-2-(3,4-difluorophenyl)pyrimidine according to claim 1.
3. 5-Propyl-2-(3,4-difluorophenyl)pyrimidine according to claim 1.
4. 5-Butyl-2-(3,4-difluorophenyl)pyrimidine according to claim 1.
5. 5-Pentyl-2-(3,4-difluorophenyl)pyrimidine according to claim 1.
6. 5-Hexyl-2-(3,4-difluorophenyl)pyrimidine according to claim 1.
7. 5-Heptyl-2-(3,4-difluorophenyl)pyrimidine according to claim 1.
8. A liquid crystal composition comprising at least one first substance having liquid crystal properties and at least one second substance having the formula:

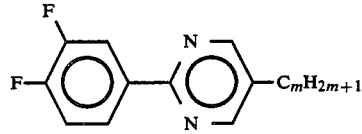

wherein m represents an integer of 1 to 8, said at least one second substance being present in an amount effective to enhence said liquid crystal properties.

9. A liquid crystal composition according to claim 8, said at least one second compound is present in an amount of 0.1 to 40 percent by weight.

* * * * *